United States Patent
Andrus

(10) Patent No.: US 10,188,423 B2
(45) Date of Patent: Jan. 29, 2019

(54) MULTI-PIECE GIMBAL RING

(71) Applicant: HeartWare, Inc., Mounds View, MN (US)

(72) Inventor: Lance Lynn Andrus, Southborough, MA (US)

(73) Assignee: HeartWare, Inc., Miami Lakes, FL (US)

( * ) Notice: Subject to any disclaimer, the term of this patent is extended or adjusted under 35 U.S.C. 154(b) by 71 days.

(21) Appl. No.: 15/393,700

(22) Filed: Dec. 29, 2016

(65) Prior Publication Data
US 2017/0189060 A1    Jul. 6, 2017

Related U.S. Application Data

(60) Provisional application No. 62/273,492, filed on Dec. 31, 2015.

(51) Int. Cl.
| | | |
|---|---|---|
| A61B 17/34 | (2006.01) | |
| A61M 1/10 | (2006.01) | |
| A61M 1/12 | (2006.01) | |

(52) U.S. Cl.
CPC ....... *A61B 17/3423* (2013.01); *A61M 1/1008* (2014.02); *A61M 1/122* (2014.02); *A61B 2017/3425* (2013.01)

(58) Field of Classification Search
CPC .............................. A61M 1/1008; A61M 1/10
See application file for complete search history.

(56) References Cited

U.S. PATENT DOCUMENTS

| | | |
|---|---|---|
| 2004/0171905 A1 | 9/2004 | Yu et al. |
| 2007/0134993 A1 | 6/2007 | Tamez et al. |
| 2013/0150654 A1 | 6/2013 | Stanfield et al. |
| 2015/0112120 A1* | 4/2015 | Andrus ............... A61M 1/1008 600/16 |
| 2015/0359952 A1 | 12/2015 | Andrus et al. |

OTHER PUBLICATIONS

International Search Report and Written Opinion dated Apr. 5, 2017, for corresponding International Application No. PCT/US2016/069136; International filed Dec. 29, 2016 consisting of 10-pages.

\* cited by examiner

*Primary Examiner* — Alyssa M Alter
(74) *Attorney, Agent, or Firm* — Christopher & Weisberg, P.A.

(57) ABSTRACT

A mounting structure for connecting a device to an organ. The mounting structure includes a mounting element defining a bore. The mounting element is adapted for mounting to an exterior surface of the organ of a living subject. The mounting element includes a collar having a deformable wall defining a main bore. A gimbal ring disposed within the main bore and within the collar is included, the gimbal ring defining a gimbal bore co-axial with the main bore and including a plurality of separate arcuate elements cooperatively disposed in a circumferential direction around the gimbal bore, the plurality of separate arcuate elements being movable toward one another to constrict the gimbal bore.

16 Claims, 3 Drawing Sheets

MULTI-PIECE GIMBAL RING

CROSS-REFERENCE TO RELATED APPLICATION

This application is related to and claims priority to U.S. Provisional Patent Application Ser. No. 62/273,492, filed Dec. 31, 2015, entitled MULTI-PIECE GIMBAL RING, the entirety of which is incorporated herein by reference.

STATEMENT REGARDING FEDERALLY SPONSORED RESEARCH OR DEVELOPMENT n/a

TECHNICAL FIELD

The present invention relates to components and methods used for mounting devices such as ventricular assist devices and associated elements to the heart of a living subject.

BACKGROUND

The heart is sometimes incapable of providing sufficient pumping capacity to meet the needs of the body. The effects of this inadequacy can be alleviated by providing a mechanical pump referred to as a mechanical circulatory support device ("MCSD"). An MCSD can be implanted to supplement the pumping action of the heart, most commonly for an extended period of time such as several years.

An MCSD is most commonly connected to the left ventricle. In this arrangement, an inlet end of the pump, or an inlet cannula connected to the inlet end of the pump, is implanted in the wall of the ventricle, such as at the apex of the ventricle. An outlet cannula is connected between the outlet end of the pump and an artery such as the aorta. MCSDs which are connected to a ventricle commonly are referred to as ventricular assist devices or "VADs." During operation, the VAD assists the heart to pump blood from the left ventricle to the aorta.

Certain MCSDs are typically connected to the heart through the use of a mounting ring, as disclosed in U.S. Published Patent Application Nos. 2004/0171905, 2007/0134993, and 2015/0112120 ("the '120 Publication"), the disclosures of which are hereby incorporated by reference herein. A mounting ring has a body and a main bore extending through the body, and also has features which can be used to attach the body to the outside of the heart wall so that the bore extends towards and away from the wall. For example, some mounting rings are equipped with a ring of fabric encircling the body, so that the mounting ring can be secured in place by suturing. Other mounting rings are equipped with barbs or other fasteners for attaching the body of the ring to the heart wall. The mounting ring is arranged so that a portion of the body defining at least part of the main bore is compressible to constrict the bore around an element of the MCSD to hold the element in place. As shown, for example, in the aforementioned U.S. Published Patent Application No. 2007/0134993 ("the '933 Publication"), the body may include a base plate which faces toward the body when the ring is installed, and a pair of generally C-shaped arms encircling the main bore. The arms have fixed ends attached to the base plate near one location on the circumference of the bore. At least one of the arms is attached to the base plate only at and near its fixed end, so that the portion of the arm remote from the fixed end is free to bend towards the opposing arm. A clamp is provided for squeezing the arms together to constrict the main bore.

The mounting ring may also incorporate an element referred to as a gimbal ring. The gimbal ring is a generally hoop-shaped element which defines a gimbal ring bore. The gimbal ring is disposed inside the main bore defined by the body. The gimbal ring may have a spherical outer surface, and the main bore may have a corresponding interior surface, so that the gimbal ring can pivot to tilt the axis of the gimbal ring bore relative to the main bore and thus relative to the body of the mounting ring. The gimbal ring typically is formed from a relatively hard polymeric material, and is provided with a slot extending through the wall of the ring at one point around its circumference. Thus, when the main bore is constricted, the mounting ring can be compressed slightly to constrict the gimbal ring bore.

A one-way valve may be mounted within the gimbal ring bore. The one-way valve typically is formed as a tubular or ring-like structure with flaps or collapsible sections which can close to occlude the gimbal ring bore.

In use of such a mounting ring, the base of the body is secured to the outside of the heart. A cruciate cut is made in the heart wall within the gimbal ring bore and a separate surgical tool is used to core a hole in the heart. The valve temporarily occludes the gimbal ring bore to prevent massive blood loss when the coring tool is removed. A pump, an inlet cannula or other element of an MCSD is, is then inserted through the interior of the valve and through the gimbal ring bore into hole into the heart. The gimbal ring can be tilted to align the axis of the MCSD element with the anatomical features of the heart. Once the MCSD element has been positioned as desired, clamp is tightened to constrict the main bore and thus constrict the gimbal ring bore to secure the MCSD element in position. The MCSD element must be secured so as to remain in place during operation, despite the loads imposed by the beating heart and by movement of the patient. While mounting rings of this type have been very effective, it is sometimes difficult to tighten the clamp sufficiently.

SUMMARY

The present invention advantageously provides for a mounting structure for connecting a device to an organ. The mounting structure includes a mounting element defining a bore. The mounting element is adapted for mounting to an exterior surface of the organ of a living subject. The mounting element includes a collar having a deformable wall defining a main bore. A gimbal ring disposed within the main bore and within the collar is included, the gimbal ring defining a gimbal bore co-axial with the main bore and including a plurality of separate arcuate elements cooperatively disposed in a circumferential direction around the gimbal bore, the plurality of separate arcuate elements being movable toward one another to constrict the gimbal bore.

In another aspect of this embodiment, the plurality of arcuate elements includes at least three arcuate elements.

In another aspect of this embodiment, a deformable element is included, the deformable element being more readily deformable than the plurality of separate arcuate elements, the deformable element being configured to connect the plurality of separate arcuate elements with one another.

In another aspect of this embodiment, the deformable element includes a resilient tube sized to be disposed within the gimbal bore.

In another aspect of this embodiment, the deformable element defines a one-way valve within the gimbal bore.

In another aspect of this embodiment, the plurality of arcuate elements is configured to attach to the resilient tube.

In another aspect of this embodiment, at least one of the plurality of separate arcuate elements is slideably engaged with at least one other of the plurality of arcuate elements to provide movement relative to one another in the circumferential direction.

In another aspect of this embodiment, the plurality of separate arcuate elements cooperatively define an exterior surface having a shape substantially in the form of a spherical segment.

In another aspect of this embodiment, each of the plurality of separate arcuate elements includes a slot at a first end and a projection at the opposite second end.

In another aspect of this embodiment, a flexible strip disposed between each of the plurality of separate arcuate elements is included.

In another aspect of this embodiment, the deformable element includes projections configured to couple with corresponding gaps in the gimbal ring.

In another embodiment, the mounting structures includes a mounting element defining a bore. The mounting element is adapted for mounting to an exterior surface of the heart of a living subject. The mounting element includes a collar having a deformable wall defining a main bore. A clamp is engaged with the collar, the clamp being arranged to deform the collar so as to constrict the main bore. A gimbal ring is disposed within the main bore, the gimbal ring defining a gimbal bore co-axial with the main bore and including a plurality of separate arcuate elements cooperatively disposed in a circumferential direction around the gimbal bore, the plurality of separate arcuate elements being movable toward one another to constrict the gimbal bore. The plurality of separate arcuate elements are movable from an unconstricted condition in which a gap is defined between adjacent arcuate element and a constricted condition in which the gaps are closed.

In another aspect of this embodiment, the main bore defines a longitudinal axis there through, and wherein the collar defines a first slot substantially parallel with the longitudinal axis.

In another aspect of this embodiment, the collar defines a second slot between the mounting element and the collar.

In another aspect of this embodiment, the plurality of separate arcuate elements are substantially rigid.

In another aspect of this embodiment, a deformable tube is included, the deformable tube being more readily deformable than the plurality separate of arcuate elements, the deformable tube being configured to connect the plurality of separate arcuate elements with one another.

In another aspect of this embodiment, the deformable element defines a one-way valve within the gimbal bore.

In another aspect of this embodiment, at least one of the plurality of arcuate elements is slideably engaged with at least one other of the plurality of arcuate elements to provide movement relative to one another in the circumferential direction.

In another aspect of this embodiment, each of the plurality of separate arcuate elements includes a slot at a first end and a projection at the opposite second end.

In yet another embodiment, the mounting structure includes a mounting ring defining a bore. The mounting ring is adapted for mounting to an exterior surface of the heart of a living subject. The mounting ring including a collar having a deformable wall defining a main bore. A clamp is engaged with the collar, the clamp being arranged to deform the collar so as to constrict the main bore. A gimbal ring is disposed within the main bore, the gimbal ring defining a gimbal bore co-axial with the main bore and including a plurality of separate arcuate elements cooperatively disposed in a circumferential direction around the gimbal bore, the plurality of separate arcuate elements being rigid and movable toward one another to constrict the gimbal bore. A deformable tube is included, the deformable tube defining a one-way valve and being more readily deformable than the plurality separate of arcuate elements, the deformable tube being configured to connect the plurality of separate arcuate elements with one another. Each of the plurality of separate arcuate elements includes a slot at a first end and a projection at the opposite second end, and at least one of the plurality of arcuate elements is slideably engaged with at least one other of the plurality of arcuate elements to provide movement relative to one another in the circumferential direction. The plurality of separate arcuate elements being movable from an unconstricted condition in which a gap is defined between adjacent arcuate element and a constricted condition in which the gaps are closed.

BRIEF DESCRIPTION OF THE DRAWINGS

A more complete appreciation of the subject matter of the present invention and the various advantages thereof can be realized by reference to the following detailed description, in which reference is made to the accompanying drawings.

DETAILED DESCRIPTION

Figure 1:
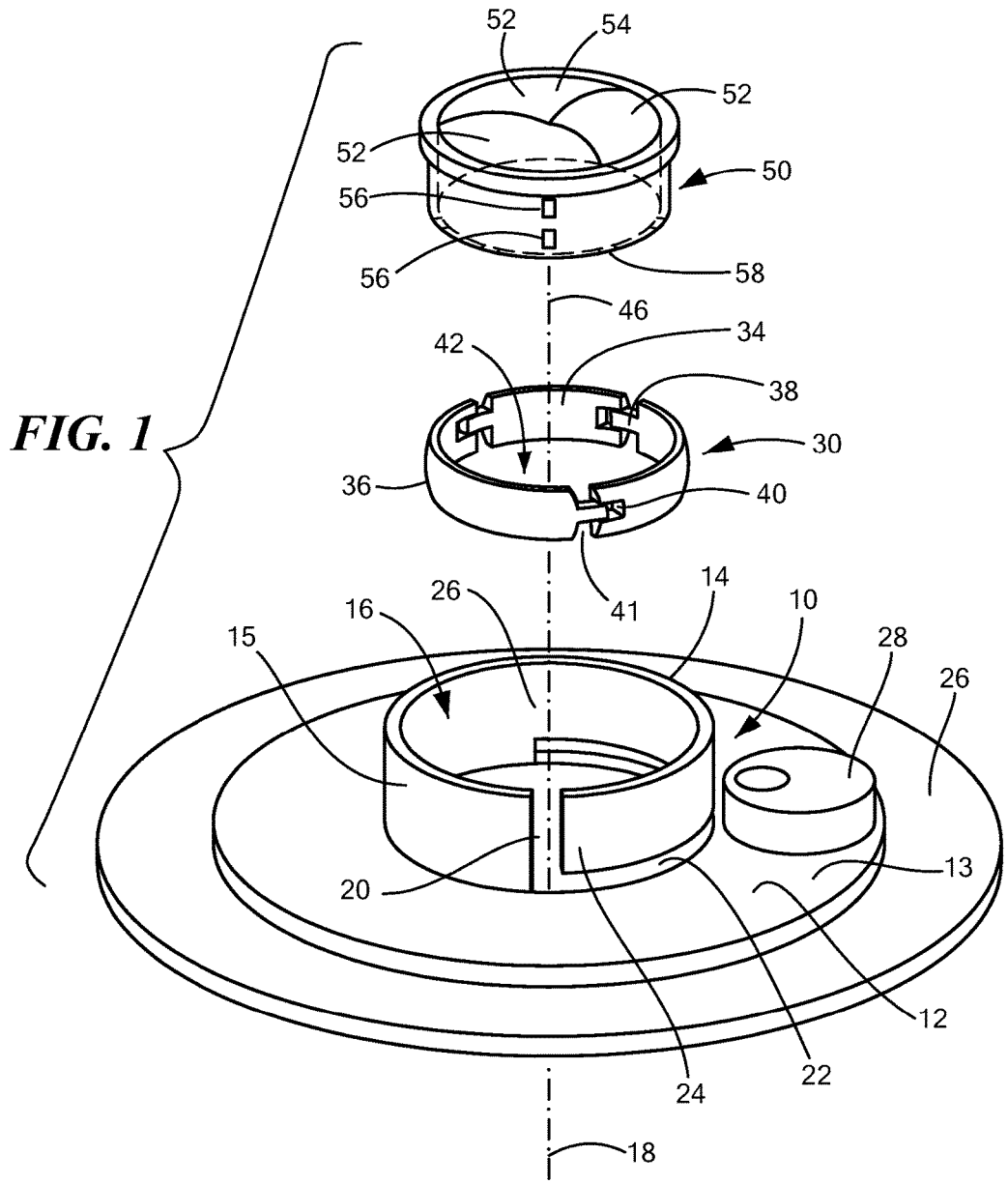
FIG. 1 is a diagrammatic exploded view of a mounting structure according to one embodiment of the invention.
Figure 2:
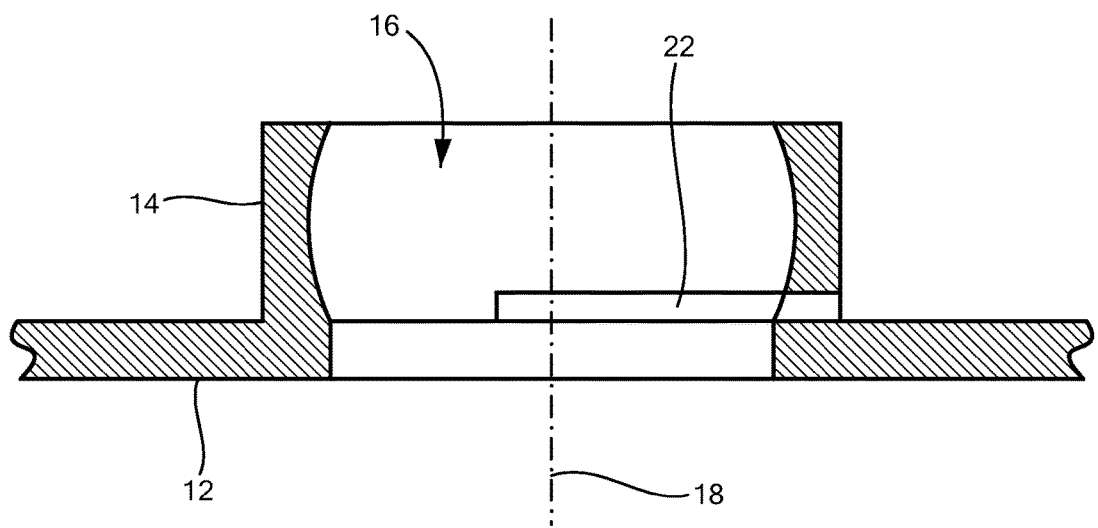
FIG. 2 is a fragmentary sectional view of an element in the structure of FIG. 1.

Referring now to the drawings in which like reference designators refer to like elements, there is shown in FIG. 1 a mounting structure constructed in accordance with the principles of the present application and designated generally as "8." The mounting structure 8 according to this embodiment includes a mounting element or body 10 in the form of a mounting ring 10. In one configuration, mounting ring 10 includes a base plate 12 and a collar 14 projecting from a proximal side 13 of the base plate 12. In one configuration, the collar 14 is cylindrical and in other embodiments may be other shapes. A main bore 16 having a main bore axis 18 extends through mounting ring 10 and is coaxial with collar 14. In one configuration, the main bore 16 extends through the entire length of the collar 14 and through the base plate 12.

The collar 14 may further define a first slot 20 extending through a wall 15 of collar 14 and extending parallel to the main bore axis 18. The wall 15 of collar 14 may be formed integrally with the base plate 12 or otherwise secured to the base plate 12 around a portion of the circumference of bore 16. The height of the wall 15 and the thickness of the wall 15 may vary in different configurations. In the configuration shown in FIG. 1, the height of wall 15 is greater than the height of the base plate 12. The collar 14 may further define a second slot 22 extending around at least a portion of the circumference of the main bore 16 configured separate at least a portion of the wall 15 of collar 14 from the base plate 12 around this portion of the circumference. Stated another way, a portion of the wall 15 of collar 14 defines a generally C-shaped arm having a free end 24 adjacent first slot 20 and a fixed end 26 that is fixed to the base plate 12 by the remainder of the collar 14. This arm may be moved toward the opposite site of the collar 14 so as to bend it inwardly and thereby constrict main bore 16. In one configuration, the interior surface of collar 14 defining the main bore 16 is substantially in the form of a zone of a sphere or spherical segment.

Continuing to refer to FIG. 1, mounting element 10 is provided with a structure suitable for attaching the base plate 12 to the exterior surface of a human or animal patient's heart. In this embodiment, that structure includes a ring of suturable material 26 secured to the periphery of base plate 12. For example, the suturable material may include a layer of a fabric or felt and may also include a layer of a tough polymeric material such as a polymer sheet. In one configuration, ring body 10 may be secured to base plate 12 by sutures (not shown) extending through apertures (not shown) in the base plate or by any other structural attachment. Other structures suitable for attaching the base plate to the heart wall include mechanical anchors such as barbs or hooks disposed around the periphery of the base plate. One scheme employing such mechanical anchors is shown in the aforementioned '120 Publication. In still other embodiments, mechanical anchors such as staples may be inserted through apertures (not shown) in the base plate.

A clamp 28 is schematically depicted as an eccentric cam that can be rotated about an axis parallel to the main bore axis 18. When clamp 28 is rotated from the position shown, a portion of the clamp 28 bears on the arm defined by wall 15 and force the free end of the arm toward first slot 20, thus constricting main bore 16. In actual practice, the clamp 28 may include additional elements such as a movable element disposed between the cam and the wall 15 of the collar. For example, the clamp 28 may be as disclosed in U.S. Published Patent Application 2015/0359952, the disclosure of which is incorporated by reference herein. Other forms of clamps may be employed. For example, a clamp may include a screw having a head carried on one portion of the collar 14 and threadably received in the opposite portion of the collar 14, so that rotation of the screw constricts the collar 14 and thus constrict the main bore 16. In yet another arrangement, clamp 28 may include a screw (not shown) threadably engaged with the base plate 12 for movement along an axis parallel to the bore axis 18. The screw may have a beveled head forming a cam surface. As the screw is advanced, the beveled head is forcibly engaged with a movable element mounted to the base plate 12, thus urging the movable element against the collar 14 to force the collar 14 into a constricted configuration when the screw is advanced. The mounting element 10 and clamp 28 may be of any construction which allows for constriction of the mounting element bore 16.

The mounting structure 8 according to one embodiment includes a gimbal ring 30. The gimbal ring 30 includes a plurality of separate arcuate pieces 32, 34, and 36. Piece 32 has a projection 38 extending generally in the arcuate or circumferential direction at one end and a slot 40 at the opposite end. Each of the other pieces 34 and 36 have corresponding projections and slots. When the pieces are in an assembled, unconstricted condition as shown in FIG. 1, the projection 38 of each piece is received in the slot 40 of an adjacent piece. In this condition, there is a gap 41 between the end of arcuate piece 32 and the end of the next adjacent arcuate piece 36, with the projection of piece 36 extending across the gap 41 and into slot 40. There is a similar gap between the end of piece 34 and the adjacent end of piece 32, and another similar gap between the end of piece 36 and the adjacent end of piece 34. The three pieces 32, 34, and 36 cooperatively define a ring having a gimbal ring bore 42, with the arcuate pieces 32, 34, and 36 being circumferentially disposed around the axis 44 of the gimbal ring bore 42. The interior wall of the gimbal ring bore 42 defined by pieces 32, 34, and 36 is substantially cylindrical. The exterior surface of the ring 30, also defined by pieces 32, 34, and 36 has a configuration complimentary to the spherical configuration defined by wall 14; the exterior surface of the ring is substantially a zone of a sphere or a spherical segment.

In the assembled but unconstricted condition shown, the end of each piece 32, 34, and 36 is free to move toward the end of the next adjacent piece 32, 34, and 36. This motion is accommodated by sliding a respective projection 38 disposed at a first end 39 of each piece 32, 34, and 36 and within a respective slot 40 disposed at a second end 43 opposite the first end 39. Thus, the ends 39 and 43 of the pieces 32, 34, and 36 are free to be displaced toward one another in the circumferential direction around axis 46, thus bringing the gimbal ring 30 to a constricted configuration in which the diameter of the gimbal ring bore 42 is reduced and the gap 41 is closed. It should be appreciated that such movement does not require deformation of the arcuate pieces 32, 34, and 36. Rather, the gaps 41 between the arcuate pieces 32, 34, and 36 are closed during movement from the conditions shown in FIG. 1 to a constricted configuration. Because the pieces 32, 34, and 36 of the gimbal ring 30 need not deform as the gimbal ring 30 is constricted, the pieces 32, 34, and 36 can be formed from a relatively rigid material such as a stiff polymer.

The mounting structure 8 according to this embodiment further includes a deformable element or tube 50 in the form of a thin tube of a rubber-like material. The tube 50 is hollow, as best seen in FIG. 1. Deformable element or tube 50 is formed integrally with three flaps 52 which form a valve. In the closed configuration shown in FIG. 1, flaps 52 cooperatively occlude the interior of the tubular member. In one configuration, pieces 32, 34, and 36 of the gimbal ring 30 are secured to the exterior surface of the tube or deformable element 50. When secured to the deformable element 50, the pieces 32, 34, and 36 are in the unconstricted or expanded configuration shown in FIG. 1. The pieces 32, 34, and 36 of the gimbal ring 30 may be secured to the deformable element 50, for example, by bonding the interior surfaces of the pieces to the wall of the deformable element 50. Optionally, deformable element 50 may have projections 56 on its exterior surface, and these projections can be engaged within the gaps 41 between adjacent pieces 32, 34, and 36 of the gimbal ring. 30. The tube 50 also optionally may have further projections 58 on its exterior surface to hold the pieces 32, 34, and 36 of the ring in a generally coplanar arrangement. In this condition, the deformable element 50 holds the pieces 32, 34, and 36 together to provide a subassembly that can be readily handled. The subassembly can be assembled to mounting element 10 by inserting the deformable element 50, with the pieces 32, 34, and 36 of the ring 30 thereon, into the main bore 16 of mounting element 10. During this process, the ring 30 may be temporarily constricted as, for example, by the operator's hand or by a fixture (not shown). Once the pieces 32, 34, and 36 of ring 30 are disposed within the bore 16, the resilience of the deformable tube 50 tends to push the pieces 32, 34, and 36 outwardly and thus restore the ring 30 to its unconstructed configuration. In this configuration, the spherical exterior surface defined by ring 30 bears on the spherical interior surface defined by the wall of main bore 18 in the mounting element 10. In this condition, the axis 46 of the ring bore 16 is generally coaxial with the axis of main bore 18.

The mounting structure 8 may be used in the normal manner. Thus, mounting element 10 is secured to the exterior surface of the heart wall as, for example, by suturing material 26 to the wall of the heart or by actuating other fastening devices (not shown). A hole is formed in the wall of the heart through valve 54 and through the gimbal ring bore 42 and main bore 18 to the surface of the heart and forming a cruciate cut. Following the cruciate cutting operation, a coring tool (not shown) may be inserted through the valve to form an open hole in the heart. The coring tool is then withdrawn and an element of an MCSD (not shown) such as a body of a pump or an inlet cannula is inserted through the valve, through the gimbal ring bore 42, and through the main bore into the heart. The MCSD element may be tilted as desired. This tilting motion is accommodated by pivoting motion of the gimbal ring 30 within the main bore 16. The spherical surface formed by pieces 32, 34, and 36 of the gimbal ring 30 provides a pivoting action and allows accurate alignment of the MCSD element with the anatomical features as desired. Once the desired alignment has been achieved, clamp 28 is actuated so as to deform the wall defining main bore 16 and constrict the main bore. This drives the pieces 32, 34, and 36 of gimbal ring 30 towards a constricted configuration in which the gaps 41 between the ends of the pieces 32, 34, and 36 are diminished, thus constricting the gimbal ring bore 42 and securely clamping the MCSD element within the gimbal ring 30 and within the mounting element 10. Because the pieces 32, 34, and 36 of the gimbal ring 30 are free to move relative to one another in the circumferential direction, they offer little or no resistance to constricting movement. This, in turn, reduces the forces that must be applied to collar 14 by clamp 28 and reduces the forces required to actuate clamp 28. During this process, the adhesive bond between the pieces 32, 34, and 36 of the gimbal ring 30 and the deformable element 50 may be broken or may remain intact. In either configuration, because the deformable element 50 is formed from a material that is more deformable than the arcuate pieces 32, 34, and 36 of the mounting ring 10, the deformable element 50 offers essentially no resistance to the constricting movement. Numerous variations of the features discussed above can be used. For example, it is not essential for the deformable element 50 connecting the arcuate pieces 32, 34, and 36 of the gimbal ring 30 to be a tubular element as shown. The deformable element 50 may be an O-ring or other structure which does not include a valve.

Figure 3:
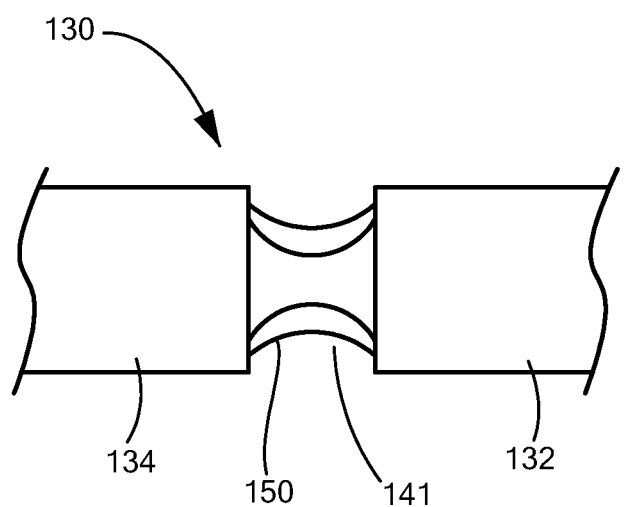
FIG. 3 is a fragmentary elevational view of a component used in a structure according to a further embodiment of the invention.

Now referring to FIG. 3, in another configuration gimbal ring 130 may include thin, flexible structures such as strips 150 extending across the gaps 141 between adjacent arcuate pieces 132 and 134 of the gimbal ring 130. These strips 150 may be formed integrally with the arcuate pieces 132 and 134. The strips 150 may sufficient strength to hold the gimbal ring 130 together during handling and assembly, but do not materially impede movement of the arcuate pieces during constriction of the gimbal ring 130.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention.

What is claimed is:

1. A mounting structure for connecting a device to an organ, the mounting structure comprising:
    a mounting element defining a bore, the mounting element being adapted for mounting to an exterior surface of the organ of a living subject, the mounting element including a collar having a deformable wall defining a main bore; and
    a gimbal ring disposed within the main bore and within the collar, the gimbal ring defining a gimbal bore co-axial with the main bore and including a plurality of separate arcuate elements cooperatively disposed in a circumferential direction around the gimbal bore, the plurality of separate arcuate elements being movable toward one another to constrict the gimbal bore, each of the plurality of separate arcuate elements includes a slot at a first end and a projection at the opposite second end, the projection of one of the plurality of separate arcuate elements being sized to be received in an adjacent respective slot of another one of the plurality of separate arcuate elements.

2. The mounting structure of claim 1, wherein the plurality of arcuate elements includes at least three arcuate elements.

3. The mounting structure of claim 1, further comprising a deformable element, the deformable element being more readily deformable than the plurality of separate arcuate elements, the deformable element being configured to connect the plurality of separate arcuate elements with one another.

4. The mounting structure of claim 3, wherein the deformable element includes a resilient tube sized to be disposed within the gimbal bore.

5. The mounting structure of claim 4, wherein the deformable element defines a one-way valve within the gimbal bore.

6. The mounting structure of claim 4, wherein the plurality of arcuate elements is configured to attach to the resilient tube.

7. The mounting structure of claim 3, wherein the deformable element includes projections configured to couple with corresponding gaps in the gimbal ring.

8. The mounting structure of claim 1, wherein at least one of the plurality of separate arcuate elements is slideably engaged with at least one other of the plurality of arcuate elements to provide movement relative to one another in the circumferential direction.

9. The mounting structure of claim 1, wherein the plurality of separate arcuate elements cooperatively define an exterior surface having a shape substantially in the form of a spherical segment.

10. A mounting structure for connecting a device to the heart, the mounting structure comprising:
    a mounting element defining a bore, the mounting element being adapted for mounting to an exterior surface of the heart of a living subject, the mounting element including a collar having a deformable wall defining a main bore;
    a clamp engaged with the collar, the clamp being arranged to deform the collar so as to constrict the main bore;
    a gimbal ring disposed within the main bore, the gimbal ring defining a gimbal bore co-axial with the main bore and including a plurality of separate arcuate elements cooperatively disposed in a circumferential direction around the gimbal bore, the plurality of separate arcuate elements being movable toward one another to constrict the gimbal bore; and the plurality of separate arcuate elements being movable from an unconstricted condition in which a gap is defined between adjacent arcuate element and a constricted condition in which the gaps are closed; at least one of the plurality of arcuate elements is slideably engaged with at least one other of the plurality of arcuate elements to provide movement relative to one another in the circumferential direction, each of the plurality of separate arcuate elements includes a slot at a first end and a projection at the opposite second end.

11. The mounting structure of claim 10, wherein the main bore defines a longitudinal axis there through, and wherein the collar defines a first slot substantially parallel with the longitudinal axis.

12. The mounting structure of claim 11, wherein the collar defines a second slot between the mounting element and the collar.

13. The mounting structure of claim 12, wherein the plurality of separate arcuate elements are substantially rigid.

14. The mounting structure of claim 10, further comprising a deformable tube, the deformable tube being more readily deformable than the plurality separate of arcuate elements, the deformable tube being configured to connect the plurality of separate arcuate elements with one another.

15. The mounting structure of claim 14, wherein the deformable element defines a one-way valve within the gimbal bore.

16. A mounting structure for connecting a device to the heart, the mounting structure comprising:

a mounting ring defining a bore, the mounting ring being adapted for mounting to an exterior surface of the heart of a living subject, the mounting ring including a collar having a deformable wall defining a main bore;

a clamp engaged with the collar, the clamp being arranged to deform the collar so as to constrict the main bore;

a gimbal ring disposed within the main bore, the gimbal ring defining a gimbal bore co-axial with the main bore and including a plurality of separate arcuate elements cooperatively disposed in a circumferential direction around the gimbal bore, the plurality of separate arcuate elements being rigid and movable toward one another to constrict the gimbal bore;

a deformable tube, the deformable tube defining a one-way valve and being more readily deformable than the plurality separate of arcuate elements, the deformable tube being configured to connect the plurality of separate arcuate elements with one another;

each of the plurality of separate arcuate elements includes a slot at a first end and a projection at the opposite second end, and at least one of the plurality of arcuate elements is slideably engaged with at least one other of the plurality of arcuate elements to provide movement relative to one another in the circumferential direction; and the plurality of separate arcuate elements being movable from an unconstricted condition in which a gap is defined between adjacent arcuate element and a constricted condition in which the gaps are closed.

* * * * *